United States Patent
Amling et al.

(10) Patent No.: US 7,289,139 B2
(45) Date of Patent: Oct. 30, 2007

(54) ENDOSCOPE READER

(75) Inventors: Marc R. Amling, Santa Barbara, CA (US); David Chatenever, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 958 days.

(21) Appl. No.: 10/095,616

(22) Filed: Mar. 12, 2002

(65) Prior Publication Data

US 2003/0174205 A1    Sep. 18, 2003

(51) Int. Cl.
*H04N 7/18*    (2006.01)
(52) U.S. Cl. .......................... 348/65; 348/61
(58) Field of Classification Search .......... 348/61, 348/65
See application file for complete search history.

(56) References Cited

U.S. PATENT DOCUMENTS

| | | | |
|---|---|---|---|
| 5,630,180 A | 5/1997 | Kusaka | 396/63 |
| 5,896,166 A | 4/1999 | D'Alfonso et al. | |
| 5,910,776 A | 6/1999 | Black | |
| 6,092,722 A | 7/2000 | Heinrichs et al. | |
| 6,141,037 A * | 10/2000 | Upton et al. | 348/65 |
| 6,295,082 B1 | 9/2001 | Dowdy et al. | |
| 6,313,868 B1 | 11/2001 | D'Alfonso et al. | |
| 6,364,827 B1 | 4/2002 | Irion et al. | |
| 6,436,032 B1 | 8/2002 | Eto et al. | 600/117 |

FOREIGN PATENT DOCUMENTS

| | | |
|---|---|---|
| DE | 197 23 442 | 2/1998 |
| EP | 59069720 | 4/1984 |
| EP | 0 534 198 | 3/1993 |
| EP | 1 155 654 | 11/2001 |
| EP | 1 155 654 A1 * | 11/2001 |
| JP | 2001-46326 | 2/2001 |
| JP | 2001-327459 | 11/2001 |
| WO | WO 97/29678 | 8/1997 |

OTHER PUBLICATIONS

Japanese Office Action, Aug. 22, 2006, 2 pages.

* cited by examiner

*Primary Examiner*—Allen Wong
(74) *Attorney, Agent, or Firm*—St. Onge Steward Johnston & Reens LLC

(57) ABSTRACT

A system for automatically setting video signal processing parameters for an endoscopic video camera system based upon characteristics of an attached endoscope, with reduced EMI and improved inventory tracking, maintenance and quality assurance, and reducing the necessity for adjustment and alignment of the endoscope and camera to achieve the data transfer.

27 Claims, 3 Drawing Sheets

ENDOSCOPE READER

FIELD OF THE INVENTION

This invention relates to endoscopic video camera systems, where the video camera electronically identifies an attached endoscope and automatically sets system parameters in accordance with certain endoscope parameters. Additionally, the endoscope is electronically identified for manipulating, (i.e., reading information from, updating and then writing information to the endoscope) for the purposes of endoscope use and maintenance, inventory tracking and control, and monitoring of various other endoscope parameters.

BACKGROUND OF THE INVENTION

An endoscope is an elongated, tubular structured medical device that is inserted into body cavities to facilitate examination by medical professionals. The endoscope includes a telescope with an objective lens at its distal end. The telescope includes an image-forwarding system, which in rigid endoscopes is typically a series of spaced-apart lenses. In flexible endoscopes, typically, the image-forwarding system is a bundle of tiny optical fibers assembled coherently.

Typically, at the proximal end of the image-forwarding system is an ocular lens that creates a virtual image for direct human visualization. Often a camera means, such as a charge coupled device (CCD) chip, is mounted to the endoscope. It receives the image and produces a signal for a video display. While surgeons can, and often do, look directly into the endoscope through an ocular lens, it is more common for them to use an attached camera and observe an image on a video screen. In conventional and video camera arrangements, the camera (hereinafter referred to as a "camera head") is usually detachably connected to the endoscope. A camera control unit (CCU) is employed to provide, among other controls, a link between the camera head and the video display.

Endoscopes come in a variety of sizes for particular applications and surgical procedures. Further, the telescope lens system may have a variety of optical properties. For example, the objective lens may include a prism whereby the image viewed is at some angle with respect to that of the axis of the telescope. Also, different endoscopes may have different fields of view (FOV). These and other variations affect the optical properties of particular endoscopes.

As above noted, the camera head is usually detachable from the endoscope, and is often conveniently constructed so as to be attachable to a variety of endoscopes having differing optical properties. For this reason, a CCU receiving a video signal from an attached camera head will need to know the endoscope optical properties in order to present an optimized image on the video monitor. Currently, the settings of the camera head and CCU are manually adjusted to the endoscope's optical properties.

It would be advantageous to simplify the task of using the endoscope and video camera system by eliminating the need to make manual adjustments to the camera head and/or CCU in order to optimize the video camera system settings for an attached endoscope.

To ensure optimal video system operation utilizing a particular endoscope, it is also necessary that the endoscope undergo periodic scheduled and unscheduled maintenance. Further, most endoscope manufacturers require their products to be maintained properly to assure reliable, accurate and precise functionality. This enhances the manufacturer's reputation and the reliance of health care professionals on the manufacturer's products. From a manufacturer's perspective, it is important that only factory authorized personnel service their products; however, it is a reality in the marketplace that some medical facilities may use unauthorized repair services. It is to a manufacturer's advantage to discourage such sub-optimal maintenance because if maintenance is performed incorrectly, medical personnel may attribute problems caused by the incorrectly performed maintenance to the product and/or manufacturing design.

Related to the maintenance of the endoscope are the usage characteristics of the endoscopes. For a manufacturer, how its products are used is valuable information. A manufacturer may want to know, for example, how often each product is used, the elapsed time of each use, the maintenance history of the product, and so on. These factors can impact future endoscope design related to durability, reliability, components and materials used in the manufacturing process.

It is known in the art to utilize electronic sensors to record operating conditions beyond the endoscope's recognized safe operating range to which it has been subjected. Peak values for conditions such as, pressure, humidity, irradiation, and/or shock or impact loads to which the endoscope has been exposed may be recorded. Upon failure of the endoscope, this information may then be utilized to determine the probable cause of the failure.

U.S. Pat. No. 5,896,166 to D'Alfonso et al. ("the '166 patent") and U.S. Pat. No. 6,313,868 to D'Alfonso et al. ("the '868 patent"), both disclose storing camera parameters and camera use characteristics in a non-volatile memory located in the camera head and transmitting the camera parameters and camera use characteristics to a camera control unit through a data coupling upon connection of the camera unit to a camera control unit. However, neither the '166 nor the '868 patents disclose a system where the endoscope has a memory device located in it, so that a single camera unit may be interchanged with a plurality of endoscopes and whereupon connection of the camera unit will automatically read the endoscope parameters and use characteristics. Further, neither the '166 nor the '868 patent discloses a system where the endoscope use characteristics can be updated to log a history of the particular endoscope use. Rather, both the '166 and the '868 patents are limited to updating only the camera unit. Still further, neither the '166 nor the '868 patent discloses a system wherein the endoscope parameters and use characteristics can be read automatically through non-contact transmission.

Another problem in the field of endoscope management is that of keeping track of the many different endoscopes used throughout the facility. There have been various approaches to keeping track of the locations and inventory of endoscopes. Simple inventory control and sign-out sheets are labor intensive and inaccurate, and, as a result, are ineffective for assuring the level of scrutiny that is required for medical equipment. Further, sign-out sheets do not allow for monitoring equipment, for example, determining whether the endoscope is functioning properly or needs maintenance.

In another example, bar codes have been used. Bar coding of equipment allows identification and locating of the equipment by reading the bar code with a portable bar code scanner. However, bar coding is ineffective when the equipment has been moved since the last time that it was scanned. Moreover, the use of bar codes can require the labor-intensive step of touring the facility with one or more portable scanners in search of endoscopes. Further, bar codes, like sign-out sheets, do not allow for the monitoring of equipment, for example, determining whether the endoscope is functioning properly or needs maintenance.

It is known in the art that energy and data transmission can take place through an inductive coupling in which high frequency coils act like a loosely coupled transformer as disclosed in U.S. Pat. No. 6,092,722 to Heinrichs et al ("the '722 patent"). The high frequency coil, when power is applied to it, produces a high frequency field, which will be imposed upon the high frequency coil of another device when brought into close proximity.

One major problem with the use of inductive coupling as disclosed in the '722 patent is that it can create unacceptable levels of electromagnetic interference ("EMI") in the operating room environment. Electronic equipment, such as the video signals transmitted from the camera head to the camera control unit, can be particularly sensitive to EMI. Therefore, to reduce the negative effects of EMI, adequate shielding should be provided. This, however, significantly adds to the cost and manufacturing time of the device. Therefore, a system that does not produce EMI is greatly desired.

Another disadvantage with the use of inductive coupling as disclosed in the '722 patent is that it necessitates the use of inductive coils both in the endoscope and the camera head adding greatly to the size and the weight of the devices. In addition to the added size and weight of the inductive coils, the necessary shielding for the EMI produced by the inductive coils will further increase the device size and weight. Endoscopes and camera heads that are lighter, smaller and easier to handle are desired.

Another disadvantage to the inductive coupling technique as disclosed in the '722 patent is because high frequency coils act like a loosely coupled transformer, both high frequency coils should be aligned one directly on top of the other in order to achieve an effective data transfer. The inductive field created by the high frequency coils is unidirectional and therefore accurate alignment of the component is important. This situation could be very frustrating for medical professionals, having to spend time trying to accurately align the camera head and endoscope to have the video system function properly. Therefore, a system that does not require precise alignment of the components is desired.

Radio frequency identification ("RFID") has been used to locate various devices and/or equipment. However, RFID used in the operating room environment has been limited due to the large power ranges required for locating the device. RFID utilized for locating purposes necessitates using a transceiver with as large a power range as is reasonable. A large power range, unfortunately, may cause receipt of the signal by unintended RFID receivers. That is, if an endoscope is in use in room A, it is undesirable to have unrelated endoscope equipment in room B "respond" to the transceiver. RFID has been limited to tracking the location of devices and/or equipment, facilitating only one-way communication from the device and/or equipment to the recording or tracking system.

Therefore, a system is needed that simplifies and optimizes endoscope and video camera usage and does not interfere with sensitive electronic equipment, encourages customers to maintain the endoscope to manufacturer's parameters and provides the endoscope manufacturer with information regarding product usage and maintenance.

SUMMARY OF THE INVENTION

The present invention is an endoscope read/write apparatus that stores and provides endoscope parameters and endoscope use history data, utilizing a detachable camera head capable of accessing the endoscope parameter data and endoscope use history data, and if required, updating and rewriting endoscope use history data to the endoscope for storage. A transponder/transceiver is affixed to the endoscope, and the endoscope transponder/transceiver is capable of transmitting and receiving radio frequency signals. The endoscope transponder/transceiver is coupled to a memory device that stores electronic representations of the endoscope parameters and endoscope use history data, and when queried, supplies the electronic representations to the endoscope transponder/transceiver. To transmit radio frequency signals for communication with the endoscope transponder/transceiver, a camera head transponder/transceiver is affixed to the camera head and set to receive the endoscope transponder/transceiver transmitted radio frequency signals. Since the present invention utilizes radio frequency transponder/transceivers, the problems associated with inductive coupling such as radiated EMI, alignment requirements, and inability to locate the device are absent.

In one advantageous embodiment of the present invention, an endoscopic video system is provided for communicating between an endoscope and a detachable camera head comprising: a first transponder/transceiver affixed to the endoscope set to transmit radio frequency signals containing electronic representations of endoscope parameters and endoscope use history data and set to receive radio frequency signals containing electronic representations of modified endoscope use history data; a second transponder/transceiver affixed to the detachable camera head set to transmit radio frequency signals containing the electronic representations of modified endoscope use history data, and set to receive radio frequency signals containing the electronic representations of endoscope parameters and endoscope use history data; a memory device coupled to the first transponder/transceiver having memory locations for storing the electronic representations of the data contained in the radio frequency signals; and a camera control unit, coupled to the camera head, for receiving and processing the electronic representations of endoscope parameters and endoscope use history data.

In another advantageous embodiment of the present invention, an endoscopic video system is provided for the transfer of data from an endoscope comprising: a transponder/transceiver affixed to the endoscope, set to transmit radio frequency signals containing electronic representations of endoscope parameters and endoscope use history data, and set to receive radio frequency signals containing electronic representations of modified endoscope use history data; and a memory device coupled to the transponder/transceiver having memory locations for storing electronic representations of the data contained in the radio frequency signals.

In yet another advantageous embodiment of the present invention, an endoscopic video system is provided for automatically adjusting to the parameters of a plurality of endoscopes, and to provide for the transfer of modified endoscope use history data comprising: a transponder/transceiver affixed to a camera head, set to transmit radio frequency signals containing electronic representations of the modified endoscope use history data, and set to receive radio frequency signals containing electronic representations of endoscope parameters and endoscope use history data; and a camera control unit, coupled to the camera head, for receiving and processing the electronic representations of endoscope parameters and endoscope use history data.

In still another advantageous embodiment of the present invention, a method is provided for communicating endoscope parameters and use characteristics from an endoscope, having a memory device and a first transponder/transceiver coupled to the memory device, to a camera control unit, and communicating modified endoscope use characteristics from the camera control unit to the endoscope comprising the steps of: storing a plurality of endoscope parameters and endoscope use characteristics in the memory device; providing a camera head with a second transponder/transceiver; coupling the second transponder/transceiver to the camera control unit; retrieving the endoscope parameters and endoscope use characteristics from the memory device; transmitting a first radio frequency signal containing the endoscope parameters and endoscope use characteristics from the first transponder/transceiver; receiving the first radio frequency signal at the second transponder/transceiver; transferring the endoscope parameters and endoscope use characteristics contained in the first radio frequency signal from the camera head to the camera control unit; transferring modified endoscope use characteristics from the camera control unit to the camera head; transmitting a second radio frequency signal containing the modified endoscope use characteristics from the second transponder/transceiver to the first transponder/transceiver; receiving the second radio frequency signal containing the modified endoscope use characteristics; and storing the modified endoscope use characteristics in the memory device memory locations.

In a further advantageous embodiment of the present invention, an endoscopic video system is provided for communicating between an endoscope and a detachable camera head comprising: a first transponder/transceiver attached to the endoscope for transmitting and receiving first data; a second transponder/transceiver attached to the detachable camera head for transmitting and receiving second data; and a memory device coupled to the first transponder/transceiver having memory locations for storing data.

The invention and its particular features and advantages will become more apparent from the following detailed description considered with reference to the accompanying drawings.

DETAILED DESCRIPTION OF CERTAIN ADVANTAGEOUS EMBODIMENTS

Figure 1:
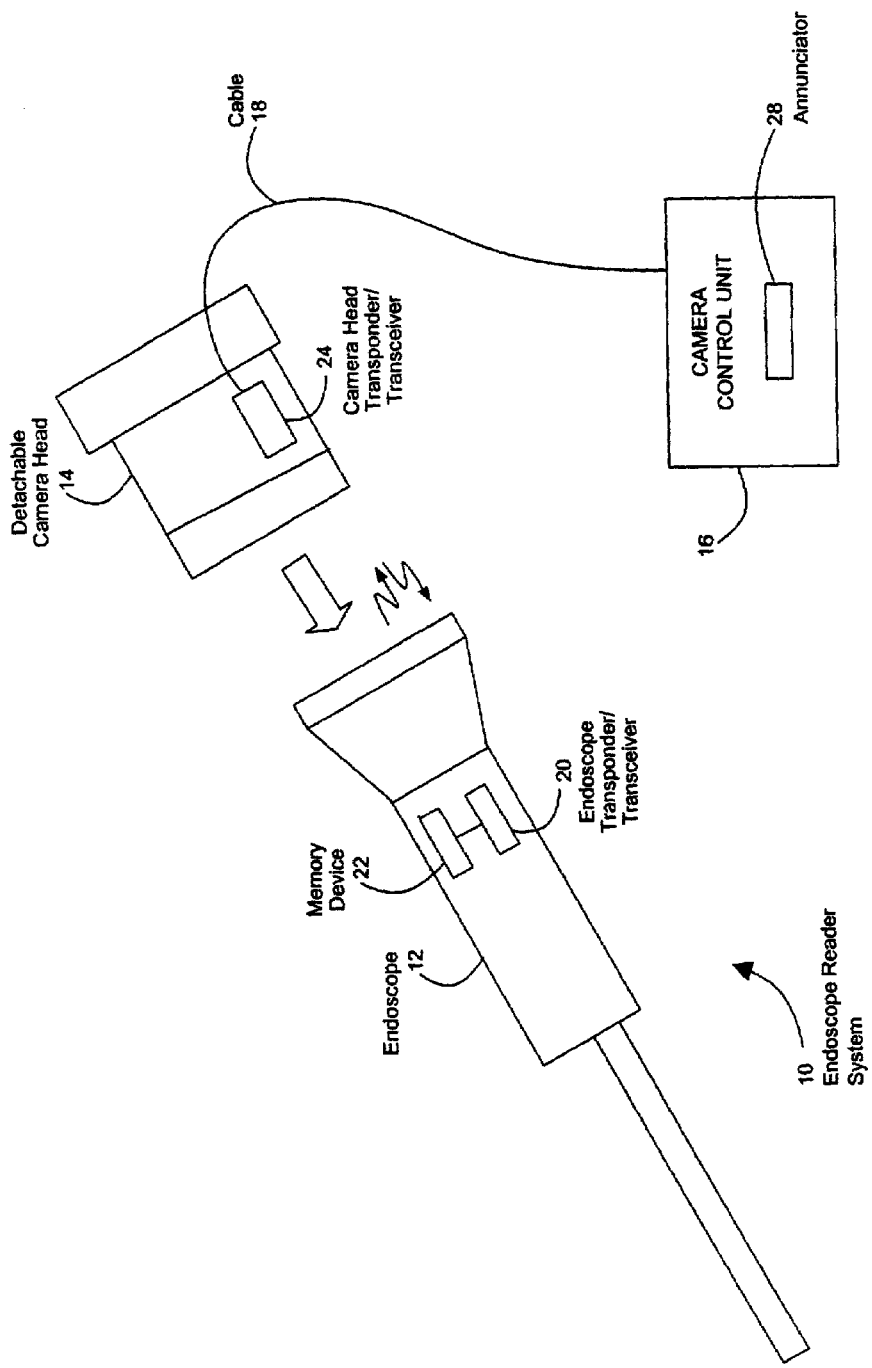
FIG. 1 is an illustration of the assembly of a detachable camera to an endoscope.

Referring to FIG. 1, an endoscopic system 10 for storing and transmitting electronic representations of endoscope characteristics is shown. In accordance with one advantageous embodiment, an endoscope transponder/transceiver 20 is mounted on an endoscope 12 and communicates with a camera head transponder/transceiver 24 mounted on a detachable camera head 14. Endoscope transponder/transceiver 20 and camera head transponder/transceiver 24 may be any type of short-range transponder/transceiver devices well known to those of ordinary skill in the art. Endoscope transponder/transceiver 20 and camera head transponder/transceiver 24 are set so that each is capable of both sending and receiving radio frequency signals to and from the other.

Endoscope transponder/transceiver 20 is coupled to a memory device 22. Memory device 22 is capable of storing and providing electronic representations of parameters of endoscope 12 to endoscope transponder/transceiver 20. Memory device 22 may be of any type that is programmable by such means as electrically, magnetically, by light frequencies or any type that is commonly known to those of ordinary skill in the art.

As mentioned above, camera head 14 is detachable from endoscope 12 and may be attached to other endoscopes. Camera head 14 is coupled to a camera control unit ("CCU") 16 by cable 18. However, camera head 14 can be coupled to CCU 16 by, for instance; a cable connection, including analog, digital or optical; or a wireless connection. Cable 18 couples CCU 16 to camera head 14 and therefore with camera head transponder/transceiver 24. An annunciator 28 may be incorporated into CCU 16 for the purpose of communicating endoscope parameters to personnel operating the endoscopic system 10. Annunciator 28 provides a means by which information concerning the endoscope is communicated to personnel operating the equipment. The annunciator may be a lamp, audible signal, alphanumeric display or other such communication device. Preferably, applicable endoscope parameters received by CCU 16 will subsequently be decoded and displayed on a video monitor for viewing by the endoscopic system 10 operator. It is contemplated that memory device 22 may be queried through the present invention by an external computer (not shown) and stored data in memory device 22 retrieved for compilation and analysis. Power for the endoscope mounted circuitry, transponder/transceiver 20 and memory device 22 may be supplied by a power signal from camera head transponder/transceiver 24 derived from a signal from camera head 14, or from an external computer.

Components such as endoscope transponder/transceiver 20, camera head transponder/transceiver 24 and memory device 22, are selected and protected such that they will not be damaged during sterilization of either endoscope 12 or camera head 14. The sterilization may comprise any or all methods of high temperature, chemical or irradiation commonly used in the field. Components employed in endoscope transponder/transceiver 20, memory device 22 and camera head transponder/transceiver 24 must not be degraded by temperatures commonly employed in autoclaves, chemicals such as gluteraldehyde or ethylene oxide, gamma radiation, or any other such sterilization techniques known to those of ordinary skill in the art.

It is also contemplated that various sensors mounted in endoscope 22 will record on memory device 22 peak values that the endoscope 22 is exposed to. This will enable manufacturers and maintenance personnel to determine reasons for endoscope failures and periods for necessary maintenance based upon usage.

It is further contemplated that the endoscopic system 10 user will be able to manually "mark" a particular endoscope with a "maintenance required" signal if it is determined by the user that maintenance of the particular endoscope is required. The "marking" can be facilitated by a button or switch locally mounted to the system. Alternatively, the "marking" may take place automatically by the system based upon predetermined criteria. The criteria may include, but is not limited to, elapsed time of use, a certain number of actuations upon receipt of exceeded peak value measurements, or an extended period of time since last maintenance. This "mark" will be transmitted by the endoscope to the CCU and will conspicuously appear on the video screen for future users to see.

The memory device 22 is write-protected such that only factory personnel and/or equipment can remove the "maintenance required" indication. This may be accomplished, for instance, by requiring specific equipment to erase the "maintenance required" indication or by means of a predetermined code that first must be input to enable the removal of the "maintenance required" indication. This will ensure that users of the endoscopic system 10 utilize only factory-authorized personnel to repair and maintain the endoscopic system 10, which will help to ensure a higher standard of service.

Figure 2:
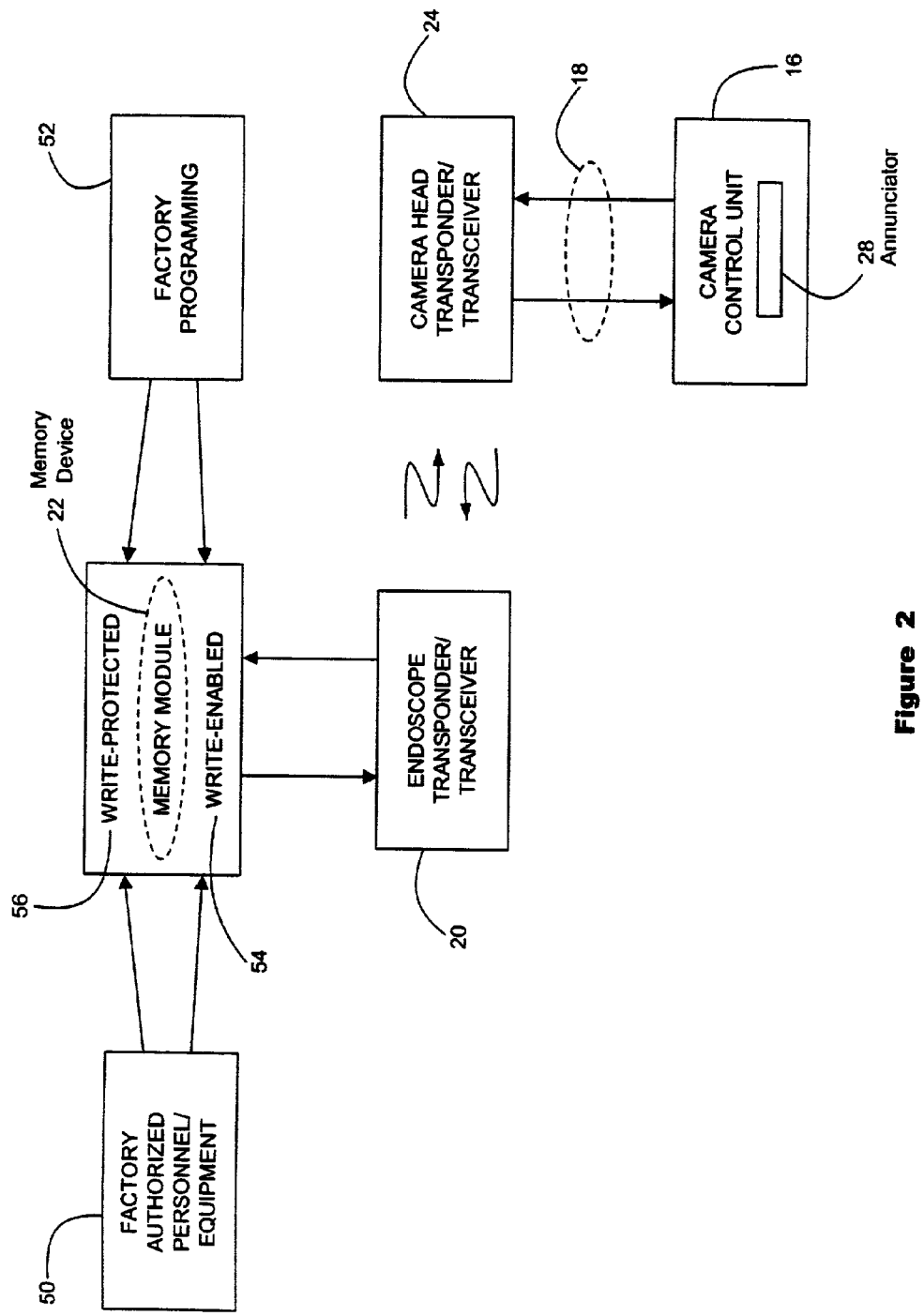
FIG. 2 illustrates the programming of the endoscope memory device and communication with the detachable camera head.

Referring to FIG. 2, memory device 22 stores and supplies electronic representations of endoscope parameters and endoscope use history data. These parameters and data provide a variety of information concerning the endoscope. Information stored in the endoscope would provide all required data for optimal use of the endoscope. In this way, the CCU 16, or other connected medical equipment, would not have to locally or remotely store and access data related to a vast array of different endoscopes. Moreover, as endoscopes are modified and/or improved, corresponding parameters and data are immediately accessible at the time of endoscope use.

The endoscope parameters are broadly classified as fixed or unchanging information. Examples of fixed or unchanging endoscope parameters may include endoscope model and serial number, image relay optics type (e.g., rod lens, fused quartz, fiber optic), endoscope size, optical properties such a field of view, signal processing data for use by the CCU 16 for video signal optimization, maintenance requirements and interval, settings information for other medical equipment (such as high intensity light sources or insufflators) which are connected and/or controlled by the CCU 16 via a communication bus or any variety of characteristics that may be useful in endoscope, video camera system and other medical equipment usage.

The endoscope use history data is broadly classified as variable or updateable. Examples of variable or updateable endoscope use history data may include, for instance, number of endoscope usages, time of each endoscope use, total time of endoscope operation, number of actuations and medical equipment (used with the endoscope) identification and settings information.

Memory device 22 locations are broadly classified as write-enabled 54 and write-protected 56. Memory device 22 can be capable of disallowing changes to memory locations until specified conditions are met. These conditions may be electrical such as requiring injection of a known signal or series of signals, or programmatic such as a password or any similar such method to prevent unauthorized alteration of the memory device locations. Write-protected locations store parameters that may be altered only during factory programming 52, or by factory authorized personnel/equipment 50. These endoscope parameters are generally, but not necessarily, fixed or unchanging as enumerated above. Write-enabled locations may be altered during factory programming 52, by factory authorized personnel/equipment 50, or with electronic representations of data received from the endoscope transponder/transceiver 20.

Endoscope transponder/transceiver 20 communicates with camera head transponder/transceiver 24 once the camera head transponder/transceiver 24 comes into close proximity. As previously described, power for the endoscope transponder/transceiver 20 is supplied from the camera head transponder/transceiver 24. Transponders and transceivers supplied with power in this manner typically have short ranges as compared to similar devices with their own power sources. It is anticipated that the effective range of transmission of the endoscope transponder/transceiver 20 and the camera head transponder/transceiver 24 may advantageously be very short. This is beneficial since an extensive transmission area could disadvantageously result in an endoscope communicating with an unrelated camera head or cause other communication problems with other equipment in the operating room.

Camera head transponder/transceiver 24 also exchanges signals with CCU 16 via cable 18. CCU 16 may present the received signals on annunciator 28. For example, data indicating that maintenance of the endoscope is required may be provided by endoscope transponder/transceiver 20 to camera head transponder/transceiver 24 which is forwarded to CCU 16 that, in turn, presents an alert to annunciator 28 that endoscope maintenance is required.

Figure 3:
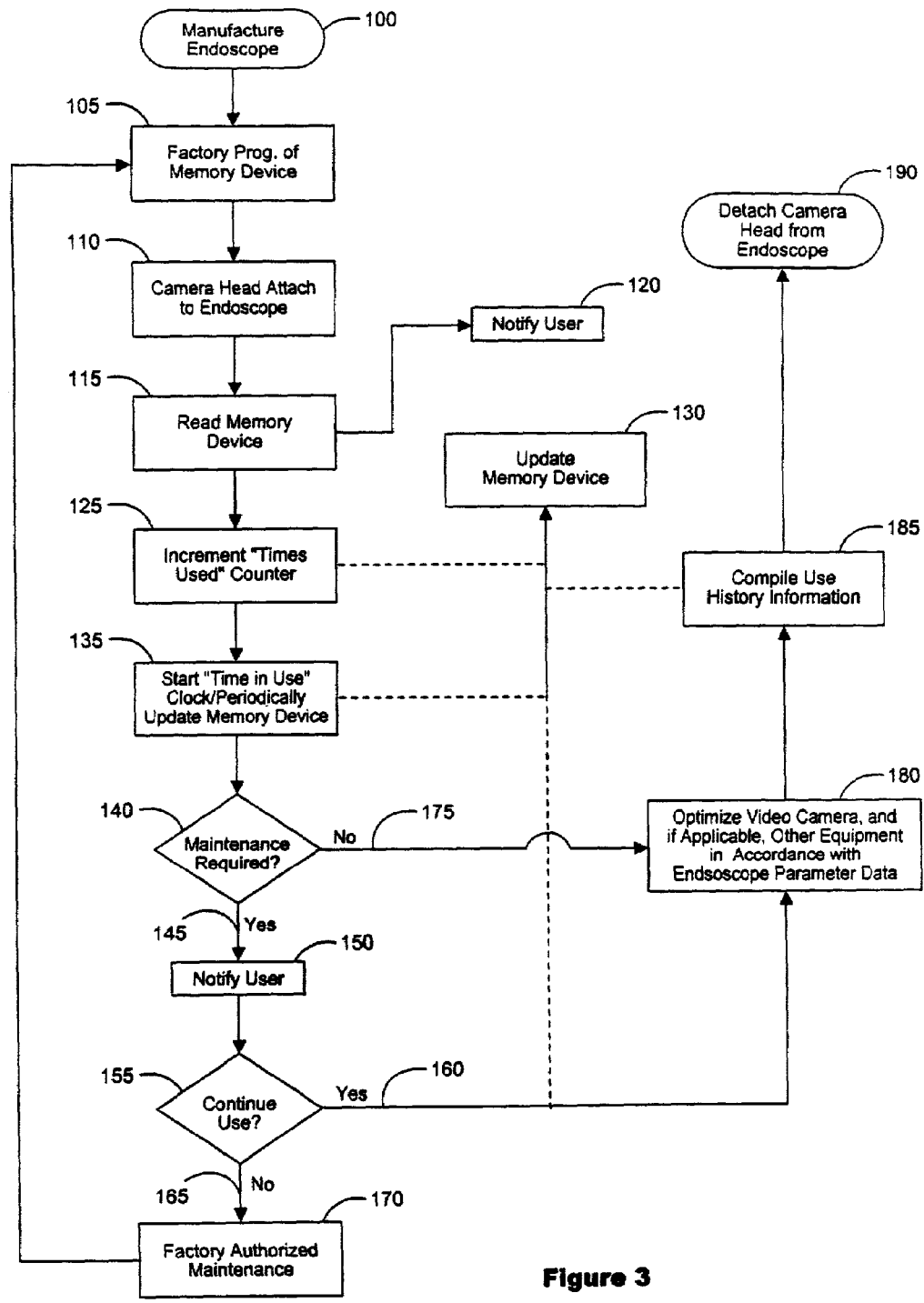
FIG. 3 illustrates a block diagram for implementing the method of the present invention.

FIG. 3 illustrates an exemplary application of the present invention. At 100, during manufacture of the endoscope, a memory device mounted in or on the endoscope is programmed with electronic representations of parameters and data specific to that particular endoscope 105. These parameters may include the optical properties, serial number, model number, maintenance schedule, required camera settings, required equipment settings, malfunction codes and other such characteristics and parameters. The memory device will have sufficient additional memory locations to store other data as described below.

Once a camera head is energized, that is, "powered on," a short-range radio frequency signal is continuously radiated from the camera head transponder/transceiver. Upon the energized camera head being attached to a particular endoscope 110, the radio frequency signal radiating from the camera head transponder/transceiver powers the endoscope transponder/transceiver. Consequently, the endoscope transponder/transceiver energizes the endoscope memory device, which provides the electronic representation of the endoscope parameters to the endoscope transponder/transceiver with the camera head transponder/transceiver receiving the radio frequency signal containing the electronic representation of the endoscope parameters from the endoscope transponder/transceiver 115. The CCU, connected to the camera head, decodes the electronic representations of the endoscope parameters and thus "identifies" the endoscope in use. Specific information can then be communicated to the system user 120, such as, but not limited to, endoscope type/model or serial number. The communication may be a visual indicator, an alphanumeric display or printout, an audio signal or any such communication technique. Preferably, the information is displayed on the system video monitor. If the endoscope attached to the camera head does not have a transponder/transceiver and programmed memory device, the video system configuration will remain unchanged.

Once the endoscope is identified and the endoscope parameters are loaded to the CCU, the CCU analysis and increments a "times used" counter (data) 125 for tracking and updating the count of how many times the endoscope was used with an endoscope reader compatible video system. The updated use count data is then written to the endoscope memory device as modified endoscope use history data by means of the camera head transponder/transceiver and the endoscope transponder/transceiver 130.

The amount of time that a endoscope is in use determines the necessity for maintenance, as well as providing statistical data for factory use in design and marketing. Concurrent with the incrementing of the "times used" counter, the CCU also starts an elapsed time ("time in use") clock 135. The elapsed time continues to accumulate as long as the camera head is attached to the endoscope. Periodically, throughout the current use of the endoscope, the CCU, by means of the camera head transponder/transceiver and endoscope transponder/transceiver, updates the endoscope memory device 130 with modified endoscope use history data containing new accumulated "time in use" data 135. In this way, the total "time in use" corresponding to a particular use of the endoscope is stored in the endoscope memory device.

Based upon endoscope parameters extracted from the endoscope memory device, the maintenance status of the endoscope 140 is determined by the CCU. The maintenance requirements' criteria, endoscope use history data and any other datum items required for the CCU to determine the current status of the endoscope was previously received by the CCU from the endoscope memory device at 115. If the CCU determines that endoscope maintenance is required 145, the maintenance related information is communicated to the user 150. The communication may be a visual indicator, an alphanumeric display or printout, an audio signal or any such communication technique. Preferably, the information is displayed on the system video monitor.

Depending upon the type of endoscope maintenance required, the user may be provided the option to continue using the endoscope 160. If the user opts to continue, information pertaining to the continuation is then written to the endoscope memory device by means of the camera head transponder/transceiver and the endoscope transponder/transceiver 130. If the user opts not to continue endoscope use 165 or the continuation option 155 is not provided to the user, it is anticipated that the endoscope will be sent for factory authorized maintenance 170. When the maintenance is completed, the memory device is updated at 105 so that the routine maintenance requirements are reset and the video system will no longer report that maintenance is required. The endoscope is again ready for camera head attachment 110 and use.

If endoscope maintenance is not required 175 at 140 or the user opts to continue using the endoscope 160 at 155, the CCU adjusts video processing settings 180 in order to optimize the video system according to endoscope parameters previously retrieved at 115. Additionally, other medical equipment, such as light sources or insufflators settings, may be optimized 180 according to endoscope parameters, as previously described.

Further information gathered, analyzed and compiled may be included in the endoscope use history data by the CCU for storage in the endoscope memory device 130. Endoscope use history data may include data on what camera head, CCU and other medical equipment was used with the endoscope (to include equipment serial numbers, model numbers, software revision numbers, etc.). Any information, which may be useful in determining how well an endoscope functioned, or under what conditions the endoscope functioned, could be included in the endoscope use history data. The endoscope use history data could later be retrieved for demographic or performance analysis purposes. An example is as follows. If a particular endoscope causes numerous CCUs to set exposure levels above a nominal value, this may indicate that the endoscope is not properly relaying images to the camera head. This CCU exposure level data would be included in the endoscope use history data and stored in the endoscope memory device. A review of the stored data would reveal this operational "trend," the endoscope could be inspected and, if necessary, repaired before a catastrophic failure occurs.

As previously described, periodically, the CCU updates the endoscope memory device 130 with modified endoscope use history data containing new accumulated "time in use" data 135. When the camera head is detached from the endoscope 190, the last accumulated "time in use" data will already have been stored in the endoscope memory device. The interval at which the "time in use" data is updated in the endoscope memory device would be frequent enough (i.e., every few minutes or every minute) to ensure the accuracy of the data prior to the camera head being detached from the endoscope.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An endoscopic video system for communicating between an endoscope and a detachable camera head comprising:
   a first transponder/transceiver affixed to the endoscope set to transmit radio frequency signals containing electronic representations of endoscope parameters and endoscope use history data and set to receive radio frequency signals containing electronic representations of modified endoscope use history data;
   a second transponder/transceiver affixed to the detachable camera head set to transmit radio frequency signals containing the electronic representations of modified endoscope use history data, and set to receive radio frequency signals containing the electronic representations of endoscope parameters and endoscope use history data;
   a memory device coupled to the first transponder/transceiver having memory locations for storing the electronic representations of the data contained in the radio frequency signals; and
   a camera control unit, coupled to the camera head, for receiving and processing the electronic representations of endoscope parameters and endoscope use history data.

2. The endoscopic video system of claim 1 wherein the endoscope parameters comprise endoscope specification data, video system configuration data and maintenance requirements data.

3. The endoscopic video system of claim 1 wherein the camera control unit automatically adjusts its operational settings in accordance with the received electronic representations of endoscope parameters.

4. The endoscopic video system of claim 1 wherein the camera control unit automatically adjusts operational settings of other medical devices in accordance with the received electronic representations of endoscope parameters.

5. The endoscopic video system of claim 1 wherein the memory locations comprise:
   write-protected memory locations; and
   write-enabled memory locations.

6. The endoscopic video system of claim 5 wherein the electronic representations of endoscope parameters are stored in the write-protected memory locations.

7. The endoscopic video system of claim 5 wherein the electronic representations of endoscope use history data are stored in the write-enabled memory locations.

8. The endoscopic video system of claim 1 wherein the camera control unit, upon receiving the electronic representations of endoscope parameters and endoscope use history data, modifies at least one endoscope use history data value indicating that a detachable camera head has been attached to the endoscope, and providing electronic representations of modified endoscope use history data to the second transponder/transceiver for transmission to the first transponder/transceiver and storage in the memory device.

9. The endoscopic video system of claim 8 wherein the camera control unit comprises a timing means for determining a time interval that the camera head has been attached to the endoscope, and the timing means providing data representative of the time interval.

10. The endoscopic video system of claim 9 wherein the electronic representations of modified endoscope use history data is altered in accordance with the data representative of the time interval that the camera head is attached to the endoscope, and the camera control unit providing electronic representations of modified endoscope use history data to the second transponder/transceiver for transmission to the first transponder/transceiver and storage in the memory device.

11. The endoscopic video system of claim 8 wherein the camera head comprises a timing means for determining a time interval that the camera head has been attached to the endoscope, and the timing means providing data representative of the time interval.

12. The endoscopic video system of claim 1 wherein the camera control unit modifies the received electronic representations of endoscope use history data in accordance with current video system operational data, providing electronic representations of modified endoscope use history data to the second transponder/transceiver for transmission to the first transponder/transceiver and storage in the memory device;
  wherein the current video system operational data comprises: current camera head, camera control unit, and other medical equipment, serial numbers, model numbers, and software revision numbers, and endoscope performance data.

13. The endoscopic video system of calim 1 wherein said memory device is positioned in or on the endoscope.

14. A method of communicating endoscope parameters and use characteristics from an endoscope, having a memory device and a first transponder/transceiver coupled to the memory device, to a camera control unit, and communicating modified endoscope use characteristics from the camera control unit to the endoscope comprising the steps of:
  storing a plurality of endoscope parameters and endoscope use characteristics in the memory device;
  providing a camera head with a second transponder/transceiver;
  coupling the second transponder/transceiver to the camera control unit;
  retrieving the endoscope parameters and endoscope use characteristics from the memory device;
  transmitting a first radio frequency signal containing the endoscope parameters and endoscope use characteristics from the first transponder/transceiver;
  receiving the first radio frequency signal at the second transponder/transceiver;
  transferring the endoscope parameters and endoscope use characteristics contained in the first radio frequency signal from the camera head to the camera control unit;
  transferring modified endoscope use characteristics from the camera control unit to the camera head;
  transmitting a second radio frequency signal containing the modified endoscope use characteristics from the second transponder/transceiver to the first transponder/transceiver;
  receiving the second radio frequency signal containing the modified endoscope use characteristics; and
  storing the modified endoscope use characteristics in the memory device memory locations.

15. The method according to claim 14 further comprising the steps of:
  providing write-protected memory locations within the memory device; and
  providing write-enabled memory locations within the memory device.

16. An endoscopic video system for communicating between an endoscope and a detachable camera head comprising:
  a first transponder/transceiver affixed to the endoscope for transmitting and receiving first data;
  a second transponder/transceiver affixed to the detachable camera head for transmitting and receiving second data; and
  a memory device coupled to the first transponder/transceiver having memory locations for storing data.

17. The endoscopic video system according to claim 16 further comprising a camera control unit, coupled to the camera head, for receiving and processing data.

18. The endoscopic video system according to claim 17 wherein the camera control unit automatically adjusts its operational settings in accordance with the received data.

19. The endoscopic video system according to claim 17 wherein the camera control unit automatically adjusts operational settings of other medical equipment in accordance with the received data.

20. The endoscopic video system according to claim 17 wherein the memory locations comprise:
  write-protected memory locations; and
  write-enabled memory locations.

21. The endoscopic video system according to claim 20 further comprising a video display, connected to the camera control unit, for viewing by a user.

22. The endoscopic video system according to claim 21 wherein the user may manually actuate a visual indication to be displayed upon the video display indicating repair and maintenance of the endoscope is required.

23. The endoscopic video system according to claim 22 wherein the visual indication is stored in the write-protected memory locations.

24. The endoscopic video system according to claim 16 wherein the first data comprises endoscope parameters.

25. The endoscopic video system according to claim 16 wherein the first data comprises endoscope use history data.

26. The endoscopic video system according to claim 16 wherein the second data comprises modified endoscope use history data.

27. The endoscopic video system of claim 16 wherein said memory device is positioned in or on the endoscope.

* * * * *